United States Patent
Hack et al.

(10) Patent No.: US 7,015,369 B2
(45) Date of Patent: Mar. 21, 2006

(54) METHOD FOR PRODUCING PROPYLENE FROM METHANOL

(75) Inventors: Markus Hack, Karben (DE); Ulrich Koss, Darmstadt (DE); Peter König, Homburg (DE); Martin Rothaemel, Frankfurt am Main (DE); Hans-Dieter Holtmann, Boenen (DE)

(73) Assignee: MG Technologies AG, Frankfurt am Main (DE)

(*) Notice: Subject to any disclaimer, the term of this patent is extended or adjusted under 35 U.S.C. 154(b) by 472 days.

(21) Appl. No.: 10/296,356

(22) PCT Filed: May 22, 2001

(86) PCT No.: PCT/EP01/05855

§ 371 (c)(1),
(2), (4) Date: Nov. 25, 2002

(87) PCT Pub. No.: WO01/92190

PCT Pub. Date: Dec. 6, 2001

(65) Prior Publication Data

US 2003/0139635 A1    Jul. 24, 2003

(51) Int. Cl.
*C07C 1/00* (2006.01)
*C07C 6/00* (2006.01)

(52) U.S. Cl. .................. 585/640; 585/302; 585/324; 585/638; 585/639

(58) Field of Classification Search ............... 585/638, 585/639, 640, 302, 324, 327
See application file for complete search history.

(56) References Cited

U.S. PATENT DOCUMENTS

| | | | |
|---|---|---|---|
| 4,404,414 A | * | 9/1983 | Penick et al. ............... 585/469 |
| 5,744,680 A | * | 4/1998 | Mulvaney et al. .......... 585/640 |
| 5,817,906 A | * | 10/1998 | Marker et al. .............. 585/640 |

FOREIGN PATENT DOCUMENTS

| EP | 0 44 8000 | 9/1991 |
|---|---|---|
| EP | 0 882692 B1 | 12/1998 |

* cited by examiner

*Primary Examiner*—Walter D. Griffin
*Assistant Examiner*—In Suk Bullock
(74) *Attorney, Agent, or Firm*—Norris McLaughlin & Marcus PA

(57) ABSTRACT

A process for producing propylene from methanol, wherein methanol vapor is reacted on a first catalyst to obtain a first vapor mixture containing dimethyl ether (DME), which is reacted on a form-selective zeolite catalyst disposed as bed in at least two series-connected shaft reactors to produce a product mixture containing propylene.

9 Claims, 2 Drawing Sheets

METHOD FOR PRODUCING PROPYLENE FROM METHANOL

This invention relates to a process of producing propylene from methanol, wherein methanol vapor is reacted on a first catalyst to obtain a first vapor mixture containing dimethyl ether (DME), and from the first vapor mixture a product mixture containing propylene is produced on a form-selective zeolite catalyst, which product mixture is cooled.

Such processes are known and described for instance in EP 0 448 000 B1 and DE 197 23 363 A1. The form-selective zeolite catalyst is disposed in a tubular reactor and is cooled indirectly, in order to dissipate heat produced.

It is the object underlying the invention to achieve a rather high content of propylene in the product mixture. At the same time, it should be possible to omit the expensive tubular reactor, in order to obtain a rather inexpensive process.

In accordance with the invention, this object is solved in the above-mentioned process in that the form-selective zeolite catalyst is disposed as bed in at least two series-connected shaft reactors, that a first partial stream of the DME-containing first vapor mixture together with steam is introduced into the first shaft reactor, a first intermediate product mixture is withdrawn from the first shaft reactor and is charged into the second shaft reactor, a second partial stream of the DME-containing first vapor mixture also being supplied to the second shaft reactor, that from the last one of the series-connected shaft reactors product mixture is withdrawn, cooled, a fraction rich in propane is separated and residual substances are obtained, which are in part gaseous and contain $C_{3+}$ hydrocarbons, and that at least part of the residual substances are recirculated into at least one of the shaft reactors. Usually, the form-selective zeolite catalyst will be disposed as bed in a maximum of four or five series-connected shaft reactors. The separation of the fraction rich in propane may be effected in a manner known per se, for instance by distillation or by adsorption.

The first catalyst on which the methanol is at first converted in part usually is likewise contained as bed in a shaft reactor, and this first catalyst may be an $Al_2O_3$ catalyst in a manner known per se. Details of the first catalyst are known from EP 0 448 000 B1 and DE 197 23 363 A1. These publications also describe the form-selective zeolite catalyst which can be used in the process in accordance with the invention. This catalyst is a pentasil-type catalyst containing protons with an alkali content of less than 380 ppm and preferably less than 200 ppm. This catalyst has a ZnO content of less than 0.1 wt-%, a CdO content of less than 0.1 wt-%, a BET surface area of 300 to 600 $m^2/g$, and a pore volume (determined by mercury porosimetry) of 0.3 to 0.8 $m^3/g$. Usually, the pressure in the vicinity of this catalyst is not more than about 0.9 bar and preferably lies in the range from 0.2 to 0.7 bar.

To the first shaft reactor, which contains the zeolite catalyst, a mixture is charged which usually comprises 10 to 40 vol-% DME (calculated dry). At the same time, a sufficient steam content of the mixture is ensured, the $H_2O$ content of the mixture lying in the range from 40 to 80 vol-%. For subsequent shaft reactors the same conditions are applicable as regards the $H_2O$ content of the mixture entering the respective reactor. Usually, at least 10% of the first vapor mixture coming from the first catalyst are supplied to each shaft reactor.

The temperatures at the inlet of the shaft reactors in which the zeolite catalyst is disposed lie in the range from 350 to 500° C. and mostly 380 to 480° C. Expediently, the shaft reactors are operated without means for indirect cooling. The production and the operation of these shaft reactors are thus simplified considerably. It is ensured that the temperature at the outlet of one or more of the shaft reactors is by 50 to 100° C. higher than at the inlet of the respective shaft reactor.

An advantageous embodiment of the process consists in that the steam-containing product mixture withdrawn from the last shaft reactor is cooled to temperatures in the range from 100 to 250° C., is compressed to a pressure in the range from 3 to 15 bar, and a compressed product mixture is produced, whose $H_2O$ content is liquefied for not more than 30 wt-%. The compressed product mixture is passed through at least one indirect heat exchanger and is cooled therein against a water phase. From the heat exchanger, a condensate-containing cooled product mixture is withdrawn, whose $H_2O$ content is liquefied for at least 80 wt-% and whose temperature is by 20 to 150° C. lower than at the inlet of the heat exchanger. In this way, heat of condensation is transferred to the water phase. From the cooled product mixture containing condensate a water phase is separated, and this water phase is recirculated to the indirect heat exchanger, where the water phase wholly or largely evaporates. The steam produced is at least partly introduced into the first shaft reactor.

Embodiments of the process will be explained with reference to the drawings, in which.

Figure 1:
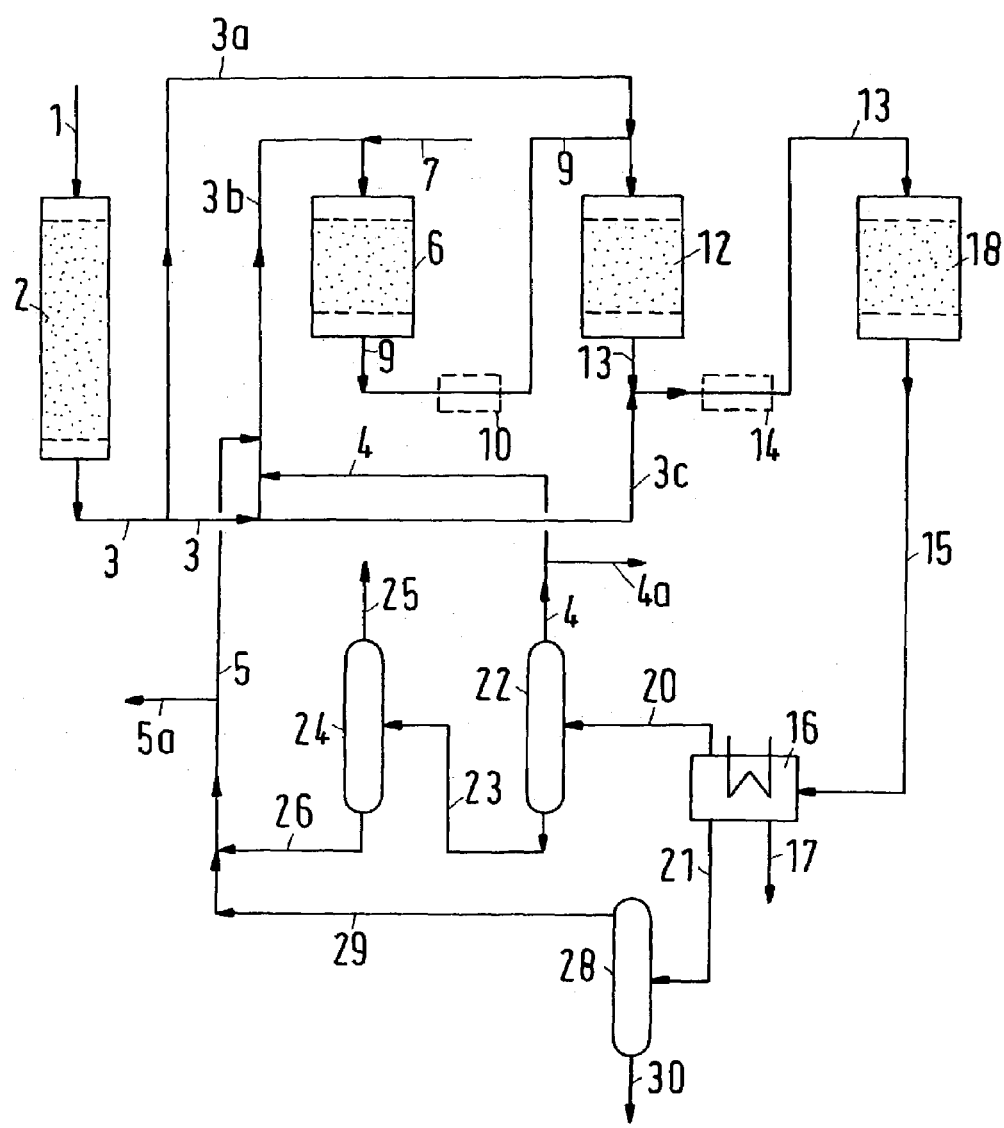
FIG. 1 shows the flow diagram of the first process variant.

As shown in FIG. 1, the methanol vapor to be reacted, which usually has temperatures in the range from 200 to 350° C., is supplied via line (1) and passed through the bed of the first catalyst (2). On the first catalyst, which consists for instance of granular $Al_2O_3$, a first exothermal conversion takes place, and in line (3) a first vapor mixture is obtained, which usually contains at least 50 vol-% DME and in addition methanol and steam. The temperature of line (3) lies in the range from 350 to 450° C. The vapor mixture of line (3) is divided into lines (3a), (3b), and (3c). The partial stream in line (3b) is also referred to as "first partial stream", and the one in line (3a) is referred to as "second partial stream".

Together with residual substances from lines (4) and (5), which are supplied in the cooled condition, the mixture of line (3b) is introduced into the first shaft reactor (6), which contains a bed of the form-selective zeolite catalyst. Steam is supplied via line (7). It is ensured that the temperature of the mixture entering the catalyst bed in the reactor (6) lies in the range from 350 to 500° C. and preferably 380 to 480° C. On the catalyst in the reactor (6), exothermal conversion reactions take place, and in line (9) a first intermediate product mixture is obtained with temperatures in the range from 400 to 600° C. If necessary, this mixture can be passed through an indirect cooler (10), which is not required in all cases and in the drawing is indicated in broken lines.

To the mixture of line (9) the partial stream from line (3a) is added, which here is also referred to as "second partial stream". The further reaction is effected in the second shaft reactor (12), which likewise contains a bed of the form-selective zeolite catalyst. The process conditions in the reactor (12) are about the same as in the reactor (6), and this is also true for the third shaft reactor (18). From the reactor (12) a second intermediate product mixture is obtained via line (13), to which second intermediate product mixture the third partial stream from line (3c) is added. Here as well, the mixture in line (13) can be passed through an indirect cooler (10), if necessary.

The mixture of line (13) is passed through the third shaft reactor (18), which in the present case is the last one of the series-connected shaft reactors, which contain a zeolite catalyst as bed. The product mixture withdrawn via line (15) usually has a propylene content, calculated dry, of 40 to 60 vol-% and in addition contains other substances which here are also referred to as residual substances.

The mixture of line (15) is first subjected to a cooling (16), and there is obtained a condensate rich in water, which condensate is discharged via line (17). Gaseous and vaporous substances are withdrawn via line (20), and a liquid mixture is discharged via line (21). The gases and vapors which also contain the desired propylene are charged into a first column (22), gases are separated and are recirculated via line (4), as described. The bottom product of column (22) flows through line (23) into a second column (24), from the top of which a fraction rich in propylene with a propylene content of usually at least 80 vol-% is withdrawn through line (25). The bottom product (mostly $C_{4+}$ hydrocarbons) leaving column (24) via line (26) is recirculated via line (5). The residual substances of lines (4) and (5) may also partly be added to the mixtures of line (3a) and/or line (3c). Excesses are removed through lines (4a) and (5a).

The liquid mixture of line (21) flows into the third column (28), from which a light $C_{5+}$ fraction is separated and is recirculated via line (29) and through line (5). The heavy constituents, usually petroleum hydrocarbons, are withdrawn through line (30) and are removed from the process.

Figure 2:
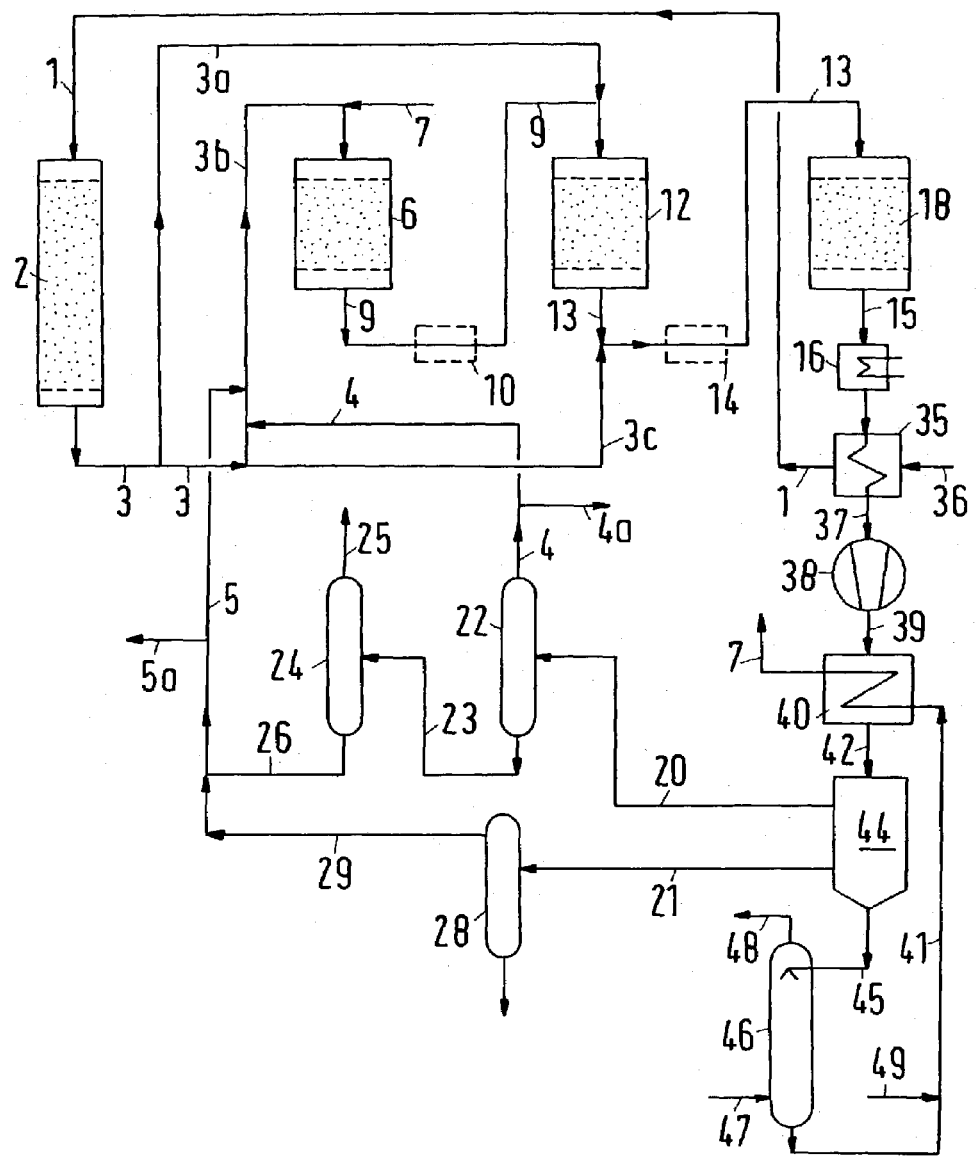
FIG. 2 shows the flow diagram of a second process variant.

In the process of FIG. 2 there is utilized the heat content of the product mixture which comes from the last shaft reactor (18) via line (15) and usually has temperatures in the range from 400 to 600° C. First of all, the product mixture releases part of its heat in the heat exchanger (16) and then in the preheater (35), to which liquid and/or vaporous methanol is supplied through line (36). From the preheater (35), methanol vapor with temperatures in the range from 200 to 350° C. is withdrawn via line (1) and is passed through the bed of the first catalyst (2). With temperatures of 100 to 250° C., the product mixture which also contains steam flows through line (37) to a compressor (38) and at the outlet thereof in line (39) has a pressure of 3 to 15 bar and for economic reasons mostly not more than 10 bar; the temperature lies in the range from 130 to 250° C. The steam of the mixture in line (39) is not yet or hardly condensed, and not more than 30 wt-% and preferably not more than 10 wt-% of the $H_2O$ content are liquefied already.

In the indirect heat exchanger (40), the product mixture of line (39) is further cooled, a water phase serving as cooling medium, which water phase is supplied via line (41). The water phase wholly or largely evaporates and the steam produced is discharged via line (7); the temperature lies between 100 and 200° C., and the pressure lies between 0.1 and 10 bar. This line (7) opens into line (3b), which for a better clarity has not been represented completely.

The product mixture coming from the heat exchanger (40) via line (42) is partly condensed, and at least 80 wt-% of the $H_2O$ content are liquefied. The temperatures in line (42) are by 20 to 150° C. and mostly 30 to 120° C. lower than in line (39), and the pressure has also decreased by 0.1 to 10 bar. For being separated, the product mixture of line (42) is charged into a separator (44), from which a water phase is withdrawn via line (45) and a liquid mixture containing petroleum hydrocarbons is withdrawn via line (21). Gases and vapors which also contain the desired propylene escape via line (20). The water phase of line (45) can be recirculated to the heat exchanger (40) through line (41). In the present case, it is charged into the stripper (46), so that by means of stripping gas (e.g. nitrogen) from line (47) low-boiling hydrocarbons (e.g. $C_2$ hydrocarbons) can be removed through line (48). The stripped water phase flows back to the heat exchanger (40) via line (41), fresh water is supplied via line (49). Moreover, the explanations given in conjunction with FIG. 1 are applicable.

EXAMPLE 1

There is employed a plant corresponding to FIG. 1 of the drawing. The data given below are calculated in part.

To the first catalyst (2), which consists of granular $AL_2O_3$, methanol vapor heated to 280° C. is supplied, and in line (3) a vapor mixture of 382° C. is obtained, which consists of 32 vol-% methanol, 34 vol-% DME, and 34 vol-% steam. This vapor mixture is divided into lines (3a), (3b) and (3c) in a ratio of 1:1.3:1.8. The weight ratio of the vapor mixture in line (3b) to the steam supplied through line (7) is 1:4. The mixture entering the first shaft reactor (6) has a temperature of 435° C. and a pressure of 1.8 bar. The form-selective zeolite catalyst of the pentasil type, which is used in the shaft reactors (6), (12) and (18), has an alkali content of 100 ppm, a content of ZnO+CdO of 0.05 wt-%, a BET surface area of 460 $m^2/g$, and a pore volume of 0.4 $m^3/g$. In all three shaft reactors, a space velocity of 1 kg methanol equivalent per kg catalyst and per hour (1 mol DME=2 mol methanol equivalent) is employed.

The mixture in line (9) has a temperature of 495° C., the temperature in the inlet of the shaft reactor (12) is about 440° C., and the shaft reactor (18) has the same inlet temperature. From the product mixture of line (15), process water (17) is separated by cooling (16), and the gaseous constituents are supplied through line (20) to column (22). The further procedure is as described in conjunction with the drawing. 10% each of the amounts flowing in lines (4) and (5) are withdrawn through lines (4a) and (5a).

Through line (29), 80% of the convertible $C_5$ to C8 olefins are withdrawn, and naphtha is obtained in line (30). The gas mixture of line (4) comprises 40 vol-% ethylene, 30 vol-% methane and for the rest ethane, $H_2$ and CO. The mixture of line (26) comprises 50 vol-% butene and 30 vol-% butane, and for the rest chiefly pentene and pentane. 58 vol-% of the mixture of line (29) consist of $C_5$ to $C_8$ olefins and for the rest of paraffin hydrocarbons.

70 mol-% of the methanol used make the product stream of line (25); it comprises 97 vol-% propylene. 26 mol-% of the methanol used are discharged as naphtha through line (5a), and 4 mol-% provide heating gas in line (4a). After a start-up phase, the steam supplied via line (7) can be reduced by one fourth.

EXAMPLE 2

The procedure substantially is as in Example 1, but the product mixture of line (15) is treated further as described in FIG. 2. The stripper (46) is omitted, lines (45) and (41) are connected with each other, the make-up water of line (49) is omitted. Important data can be taken from the following table:

| Reference numeral | 37 | 39 | 42 | 7 | 20 | 21 |
|---|---|---|---|---|---|---|
| Temperature (° C.) | 180 | 185 | 120 | 113 | 120 | 120 |
| Pressure (bar) | 1.3 | 5.5 | 4.5 | 1.6 | 2.0 | 2.0 |

The invention claimed is:

1. A process of producing propylene from methanol, wherein methanol vapor is reacted on a first catalyst to obtain a first vapor mixture containing dimethyl ether (DME), and from the first vapor mixture a product mixture containing propylene is produced on a form-selective zeolite catalyst, wherein the form-selective zeolite catalyst is disposed as bed in at least two series-connected shaft reactors, a first partial stream of the DME-containing first vapor mixture together with steam is introduced into the first shaft reactor, from the first shaft reactor a first intermediate product mixture is withdrawn and charged into the second shaft reactor, a second partial stream of the DME-containing first vapor mixture also being supplied to the second shaft reactor, a steam-containing product mixture is withdrawn from the last of the series-connected reactors and cooled, a fraction rich in propane is separated therefrom and residual substances are obtained, which are in part gaseous and contain $C_{3+}$ hydrocarbons, and at least part of the residual substances are recirculated to at least one of the shaft reactors.

2. The process as claimed in claim 1, wherein said first partial stream of said first vapor mixture introduced into the first shaft reactor comprises 10 to 40 vol-% DME.

3. The process as claimed in claim 1 wherein the steam-containing product mixture withdrawn from the last shaft reactor is cooled to temperatures in the range from 100 to 250° C., compressed to a pressure in the range from 3 to 15 bar, and a compressed product mixture is produced, not more than 30 wt-% of the $H_2O$ content of which is liquefied, the compressed product mixture is passed through at least one indirect heat exchanger and is cooled therein against a water phase, a condensate-containing cooled product mixture is withdrawn from the heat exchanger 80% of the $H_2O$ content of which is liquefied and which product mixture is at a temperature which is 20 to 150° lower than the temperature at the inlet of the heat exchanger, a condensed water phase is separated from the product mixture, and this water phase is introduced into the indirect heat exchanger, and the water phase in the heat exchanger wholly or largely evaporates, and the steam thereby produced is at least partly introduced into the first shaft reactor.

4. The process as claimed in claim 3, wherein low-boiling hydrocarbons are removed from the water phase before the water phase is introduced into the indirect heat exchanger.

5. The process as claimed in claim 1 wherein three shaft reactors are connected in the series, a second intermediate product mixture coming from the second shaft reactor and a third partial stream of the DME-containing first vapor mixture are supplied to the third shaft reactor and product mixture is withdrawn from the third shaft reactor.

6. The process as claimed in claim 1, wherein the temperatures at the inlet of the shaft reactors are in the range from 350 to 500° C.

7. The process as claimed in claim 1, wherein the shaft reactors operate without means for indirect cooling.

8. The process as claimed in claim 1 wherein, in one or more of the shaft reactors the temperature at the shaft reactors the temperature at the outlet is 30 to 100° C. higher than at the inlet.

9. The process as claimed in claim 1 wherein the product mixture discharged from the last shaft reactor has a propylene content of 20 to 50 vol-%.

* * * * *

UNITED STATES PATENT AND TRADEMARK OFFICE
CERTIFICATE OF CORRECTION

PATENT NO. : 7,015,369 B2 Page 1 of 1
APPLICATION NO. : 10/296356
DATED : March 21, 2006
INVENTOR(S) : Hack et al.

It is certified that error appears in the above-identified patent and that said Letters Patent is hereby corrected as shown below:

Column 4, Line 37, "$C_5$ to C8 olefins" should read -- $C_5$ to $C_8$ olefins --

Signed and Sealed this

Eighteenth Day of March, 2008

JON W. DUDAS
*Director of the United States Patent and Trademark Office*